(12) United States Patent
Begun

(10) Patent No.: US 6,736,826 B2
(45) Date of Patent: May 18, 2004

(54) EAR HYGIENE DEVICE

(76) Inventor: Jacob Begun, 7 Hameyasdim Street, 76804, Mazkeret Batya (IL)

( * ) Notice: Subject to any disclaimer, the term of this patent is extended or adjusted under 35 U.S.C. 154(b) by 55 days.

(21) Appl. No.: 09/734,574

(22) Filed: Dec. 13, 2000

(65) Prior Publication Data

US 2001/0001828 A1 May 24, 2001

Related U.S. Application Data

(63) Continuation-in-part of application No. 09/214,123, filed as application No. PCT/IL96/00035 on Jul. 4, 1996, now abandoned.

(51) Int. Cl.[7] .............................................. A61F 11/00
(52) U.S. Cl. ................................................... 606/162
(58) Field of Search ........................... 606/162, 106, 606/107, 110, 113, 160

(56) References Cited

U.S. PATENT DOCUMENTS

| | | |
|---|---|---|
| 147,660 A | 2/1874 | Leiner |
| 1,658,801 A | 2/1928 | Condren |
| 2,096,162 A | 10/1937 | Daley |
| 2,569,234 A | 9/1951 | Finck |
| 2,583,750 A | 1/1952 | Runnels |
| 3,203,418 A | 8/1965 | Johnston |
| 4,981,143 A | 1/1991 | Sakita et al. |
| 5,334,212 A | 8/1994 | Karell |
| 5,348,023 A | 9/1994 | McLucas |
| 5,632,756 A * | 5/1997 | Kruglick ..................... 606/160 |
| 5,715,850 A * | 2/1998 | Markgraaf ................... 132/333 |
| 5,888,199 A * | 3/1999 | Karell et al. ................ 606/162 |
| 6,033,417 A * | 3/2000 | Tseng .......................... 606/106 |

FOREIGN PATENT DOCUMENTS

| | | |
|---|---|---|
| DE | 857 128 | 11/1952 |
| DE | 36 33 585 A1 | 7/1988 |
| DE | 93 08 737 | 9/1993 |
| EP | 0 744 168 A2 | 11/1996 |
| FR | 2 551 657 | 3/1985 |
| GB | 2 204 496 A | 11/1988 |
| WO | WO 96/14033 | 5/1996 |

* cited by examiner

Primary Examiner—Ismael Izaguirre
(74) Attorney, Agent, or Firm—Browdy and Neimark, P.L.L.C.

(57) ABSTRACT

A double-headed implement insertable by its user into an ear canal, one head (X) functioning to scrape wax from the surface of the canal, the other head (Y) functioning to remove water therefrom. The implement is formed by a handle shank having at one end a loop defining the X-head and at the opposite end a loop defining the Y-head. The X-head loop is provided with an inwardly-directed scraper which when the implement is manipulated by a user to cause this loop to sweep over and massage the surface of the ear canal, it then scrapes off the wax therefrom and collects it for removal from the canal. The Y-head loop has mounted therein a flat insert of absorbent material which when this head sweeps over the surface of the ear canal, absorbs water therefrom which causes the insert to swell like a sponge to store the absorbed water so that it can be removed from the canal.

25 Claims, 4 Drawing Sheets

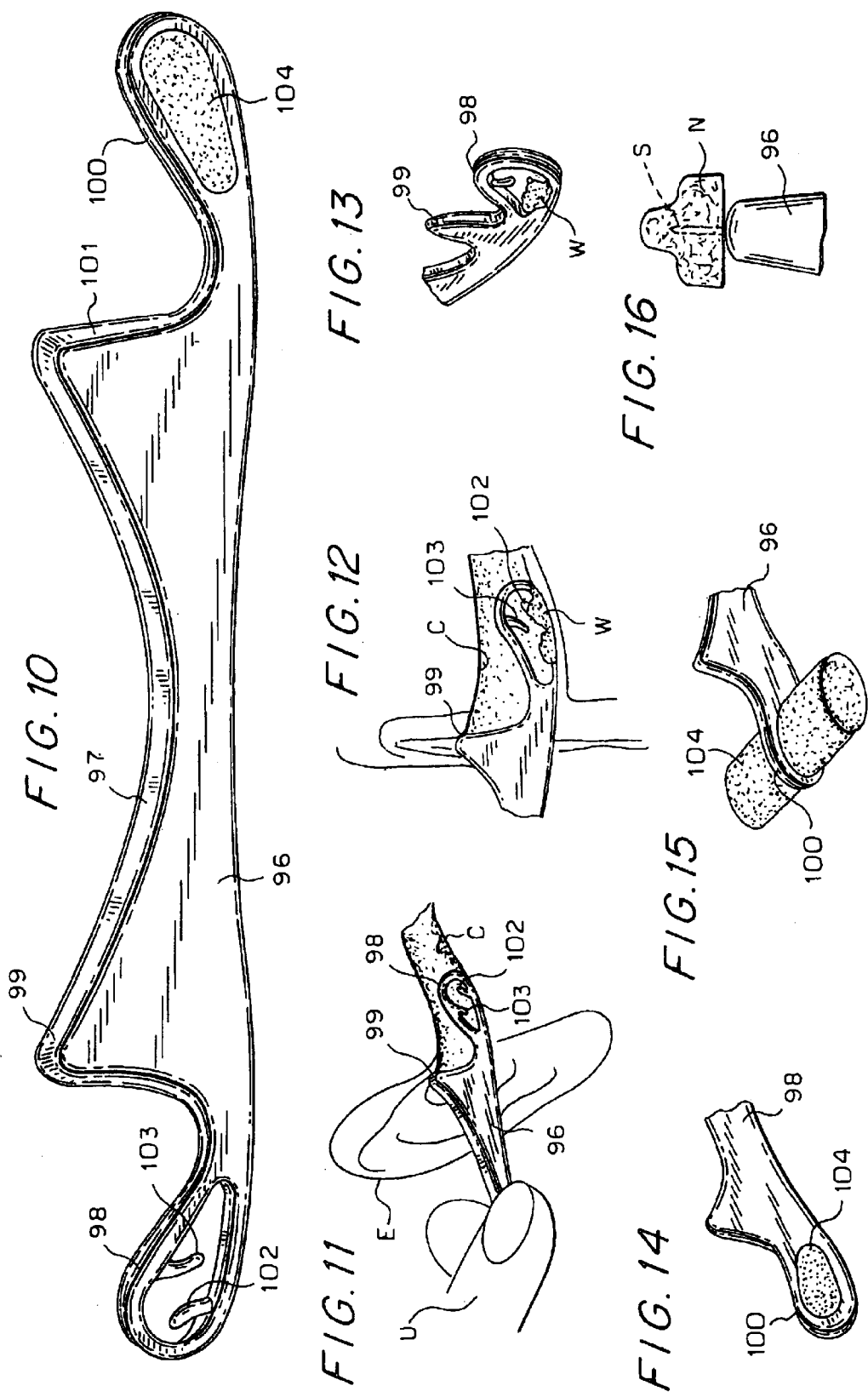

EAR HYGIENE DEVICE

RELATED APPLICATION

This application is a Continuation-In-Part of my U.S. patent application Ser. No. 09/214,123 filed Dec. 28, 1998 now abandoned entitled "Ear and Nose Hygiene Device", the entire disclosure of which is incorporated herein by reference, which is the national stage of PCT/IL96/00035, filed Jul. 4, 1996.

BACKGROUND OF THE INVENTION

Field of the Invention

The human ear consists of three major components: an external or outer ear, a middle ear and an inner ear. The concern of the present invention is with the hygiene of the outer ear which is composed of an auricle or ear lobe, an auditory canal and an ear drum which is responsive to sounds entering the auricle and conveyed by the canal to the ear drum.

Wax is exuded from glands in the cartilage portion of the ear canal, the wax acting to protect the ear from infection and to prevent foreign particles from reaching the eardrum. Ear infections often result from bacteria-laden water trapped in the ear canal.

The most commonly used ear hygiene implement is the swab, this being formed by a wad of soft cotton wound about one end of a small stick. Despite its popularity, most ear specialists interdict the use of swabs, for while a swab is effective in removing some wax from the surface of an ear canal, it also acts to push surface wax further into the ear canal. Hence repeated use of swabs ultimately acts to plug the ear canal and in some cases to entrap water therein.

The configuration of an ear canal is such that once water enters the canal in the course of swimming or bathing activity, it then becomes difficult for the water to escape. The presence of water in the canal, as previously noted, is a common cause of ear infections and may lead to a loss of hearing.

Of prior art interest is the ear wax-removing implement disclosed in U.S. Pat. No. 147,660, the implement consisting of a twisted wire handle having a loop at either end to which a swab is attached. Of greater prior art interest is the wax extractor disclosed in the U.S. Pat. No. 5,334,212 to Karell in which the implement is in the form of a loop-shaped curette.

A curette is an edged instrument which by repeated strokes acts to scrape the surface engaged thereby. But when the surface to be scraped is that of an ear canal having a relatively soft skin, a curette cannot safely be used to scrape wax therefrom, for the outer edge of the curette loop may scratch this surface in the process of scraping wax therefrom.

Also of prior art interest is the British patent GB 2204496 to McMillan which disclosed an implement for scraping exudate from a cervix and collecting this exudate. The McMillan implement is provided with a loop having an outer scraping edge, as in a curette, and inner projections which collect the exudate scraped from the surface of the cervix.

In a wax-scraping implement in accordance with the invention which includes a loop, scraping is effected not by the loop whose surface is smooth and glides over the surface of an ear canal, but by a scraper which projects inwardly from the loop and is enclosed by the loop.

SUMMARY OF THE INVENTION

In view of the foregoing, the main object of this invention is to provide an ear hygiene implement adapted to scrape wax from the surface of the ear canal in which the implement is inserted without scratching, cutting or otherwise injuring the surface and without ramming the wax more deeply into the canal.

Among the significant advantages of an implement in accordance with the invention are the following:

A. the implement is safe to use, for it includes a guard which limits the extent that the implement can be inserted into an ear canal.

B. The implement which includes a shank having a loop at one end thereof is molded of a single piece of flexible, biocompatible plastic material which is repeatedly bendable yet virtually unbreakable; hence regardless of how vigorously it is manipulated, the loop of the implement which is then in the ear canal will not break off from its shank.

C. The plastic implement is disposable and can be mass-produced at a relatively low cost.

D. The implement is anatomically designed to accommodate the human ear, yet is aesthetically pleasing.

Briefly stated, in one preferred embodiment of the invention these objects are attained in a double-headed implement insertable by its user into an ear canal, one head (X) functioning to scrape wax from the surface of the canal, the other head (Y) functioning to remove water therefrom. The implement is formed by a handle shank having at one end a loop defining the X-head and having at the opposite end a loop defining the Y-head.

The X-head loop is provided with an inwardly-projecting scraper which when the implement is manipulated by a user to cause the head to sweep over and massage the surface of the ear canal, it then scrapes off the wax therefrom and collects it within the loop for removal from the canal. The Y-head loop has mounted therein a flat insert of absorbent material which when this head sweeps over the surface of the ear canal, absorbs water therefrom which causes the insert to swell like a sponge to store the absorbed water so that it can be removed from the canal.

Alternatively, instead of a double-headed implement in which one head is adapted to scrape wax from the surface of an ear canal and the other to absorb water therefrom, both heads can be wax-scraping heads, or both heads can be adapted to absorb water.

BRIEF DESCRIPTION OF THE DRAWINGS

For a better understanding of the invention as well as other objects and further features thereof, reference is made to the annexed drawings wherein:

FIG. 10 is an elevated view of a double-headed implement in accordance with the invention;

FIG. 11 illustrates the manner in which the wax-removing X-head of the double-headed instrument is inserted into an ear canal;

FIG. 12 shows how the X-head operates to remove wax;

FIG. 13 shows why the X-head does not shove wax on the canal surface more deeply into the canal;

FIG. 14 shows the water-removing Y-head of the double-headed implement in its initial flat state; and FIG. 15 shows the Y-head after it has absorbed water and is then in a swelled state.

FIG. 16 shows a nipple-shaped moisture absorbing head attached to one end of the shank of the implement.

DETAILED DESCRIPTION OF THE INVENTION

First Embodiment

Figure 1:
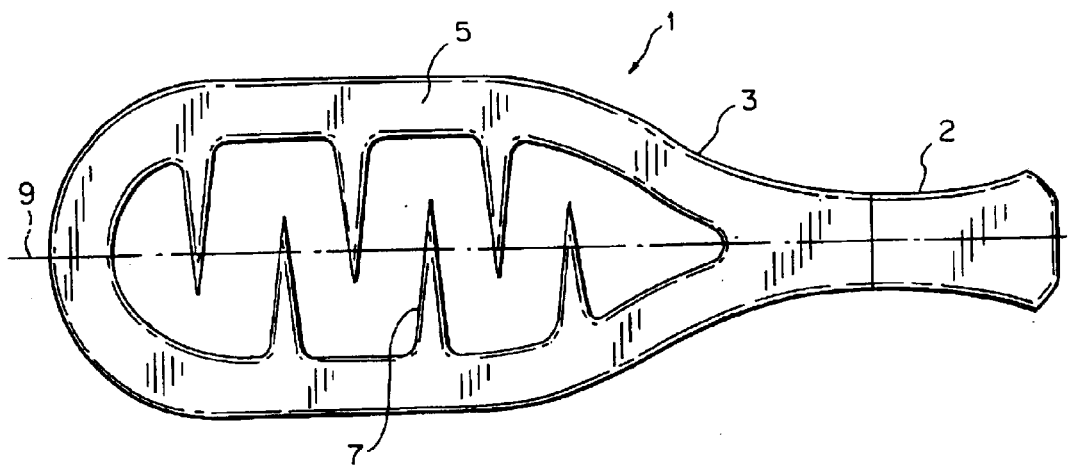
FIG. 1 shows an embodiment of a wax-removing implement in accordance with the invention in which the wax-removing member is in the form of projections extending inwardly from a loop.

Referring now to FIG. 1, shown in this figure is a wax-removing implement 1 in accordance with the invention composed of a stem 2 acting as a handle joined to a paddle-shaped loop 5 through a tapered junction 3, only a portion of the stem being shown in FIG. 1. The exterior surface of loop 5 is smooth and free of protuberances or irregularities so that friction between the loop and the ear canal when the loop is inserted therein is minimized.

Loop 5 is provided with an upper and a lower set of teeth 7 which project inwardly from the loop so that the spaced teeth in the lower set extend into the spaces between adjacent teeth in the upper set. All of the teeth 7 lie in a common plane bordered by loop 5. When, therefore, loop 5 engages the surface of the ear canal to encircle an area having a wax coating thereon, and the implement is manipulated by grasping stem 2 to sweep and massage this area, the teeth within the loop then scrape the wax off said area.

Figure 2:
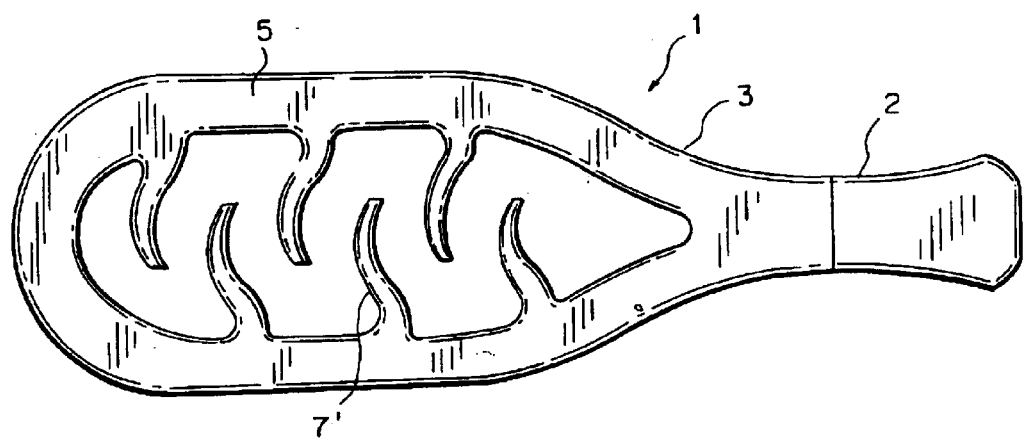
FIG. 2 illustrates a first modification of the implement shown in FIG. 1.

In the modified implement illustrated in FIG. 2, there is also an upper and a lower set of inwardly-projecting teeth 7' within a loop having a smooth exterior. However in this arrangement, teeth 7' which all lie in a common plane all have a curved, not a triangular formation.

Figure 3:
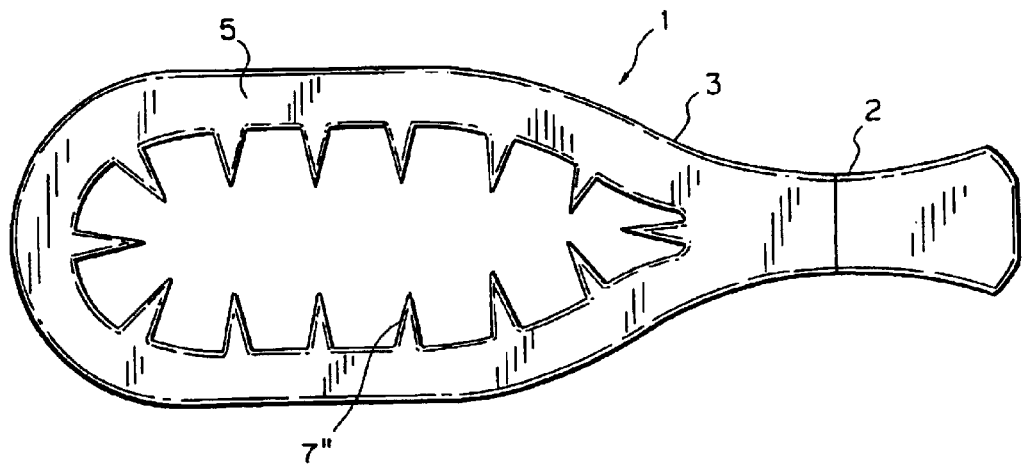
FIG. 3 illustrates a second modification.

The modified implement shown in FIG. 3 also has triangular teeth 7" inwardly projecting from loop 5. But these teeth are relatively short and therefore do not, as with the teeth in FIG. 1, have lower teeth which extend into spaces between adjacent upper teeth.

In all embodiments of implements disclosed herein, the implement is molded of high-strength, biocompatible synthetic plastic material such as polypropylene or polyethylene. The implement may be molded in one piece in which the loop is integrated with the stem or in separate pieces, in which case it is necessary to attach the stem to the loop. But in all cases, the rim of the loop is smooth so that it is slidable on the canal surface and will not scratch or otherwise injure the surface, the wax scraping action being carried out by the inwardly-projecting teeth or other wax-removing members which lie within the loop.

The strength of the implement is such that no matter how vigorously it is manipulated, the loop inserted into ear canal will not break off the stem then being grasped by the user.

The advantage gained by the use of polypropylene is that the implement can be severely and repeatedly bent without causing the loop to break off from the stem.

Second Embodiment

Figure 4:
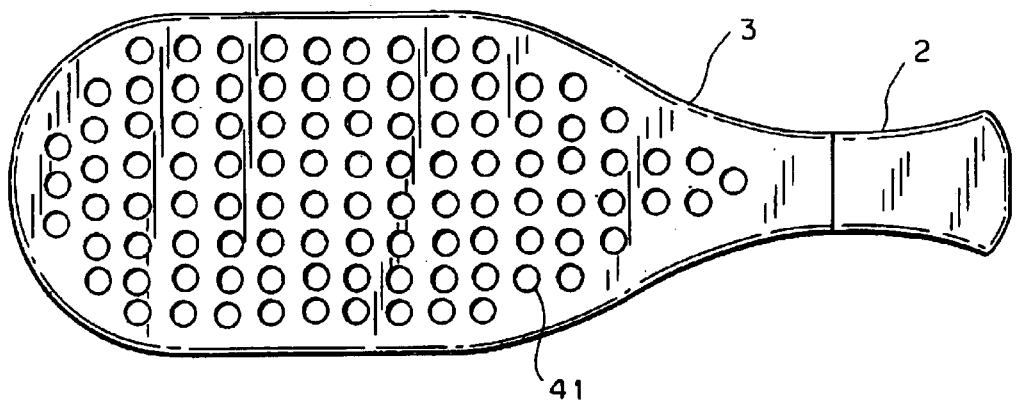
FIG. 4 shows an embodiment of a wax-removing implement in which the wax scraping member is a perforated matrix.

In the embodiment shown in FIG. 4, the implement has no clearly defined loop which in this configuration is defined by the rim at the outer edge of a paddle-shaped member. The scraper in this implement which projects inwardly from the rim is defined by a planar array of edged, round holes 41.

When the paddle-shaped loop engages an ear canal surface, the wax thereon is admitted into holes 41 and when the loop is swept over the canal surface, the wax is scraped therefrom, the scraped wax then sticking to the outer face of the implement.

Figure 5:
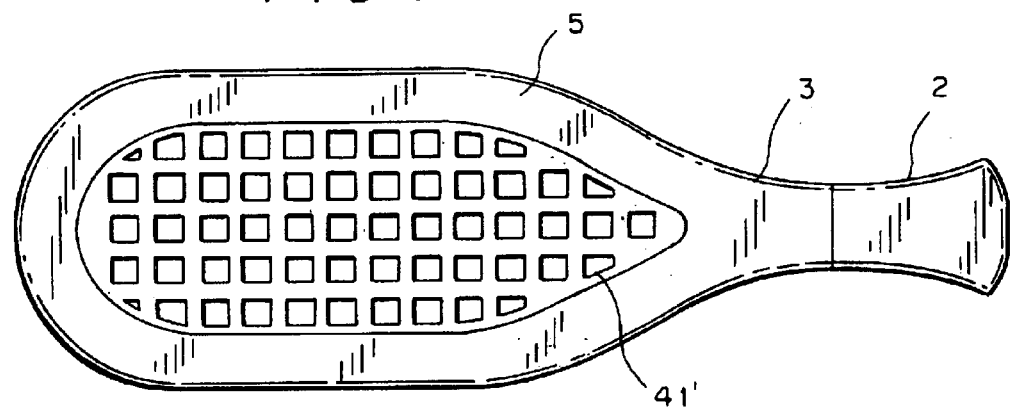
FIG. 5 is a modification of the implement shown in FIG. 4.

In the modification shown in FIG. 5, there is now a clearly defined loop 5 as in FIG. 1. But loop 5 in this instance is the rim of a paddle having an array of edged apertures 41' which are of square shape, not round as in FIG. 4. This implement scrapes off wax in the same way of the implement shown in FIG. 4. However, with the square apertures, the wax collects better on the outer face of the paddle.

Third Embodiment

Figure 6:
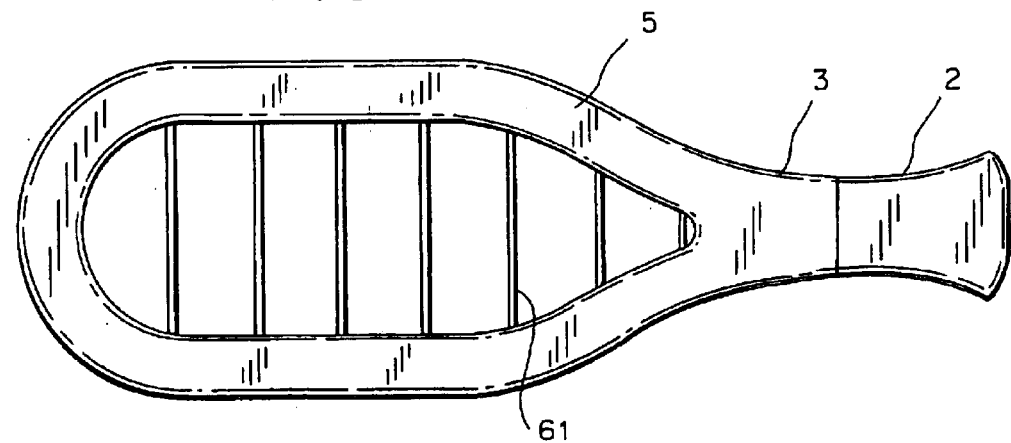
FIG. 6 shows an embodiment of the implement in which the wax-removing member is formed by parallel struts.

In this embodiment illustrated in FIG. 6 projected inwardly from loop 5 is a parallel array of edged struts 61 which act to scrape wax from the ear canal surface when the surface is swept by the loop. Again it must be noted that the loop has a smooth exterior and therefore slides on the surface of the ear canal and inflicts no injury thereto. The ear is a delicate organ and it is of the utmost importance that it not be injured by an ear cleaning implement.

Figure 7:
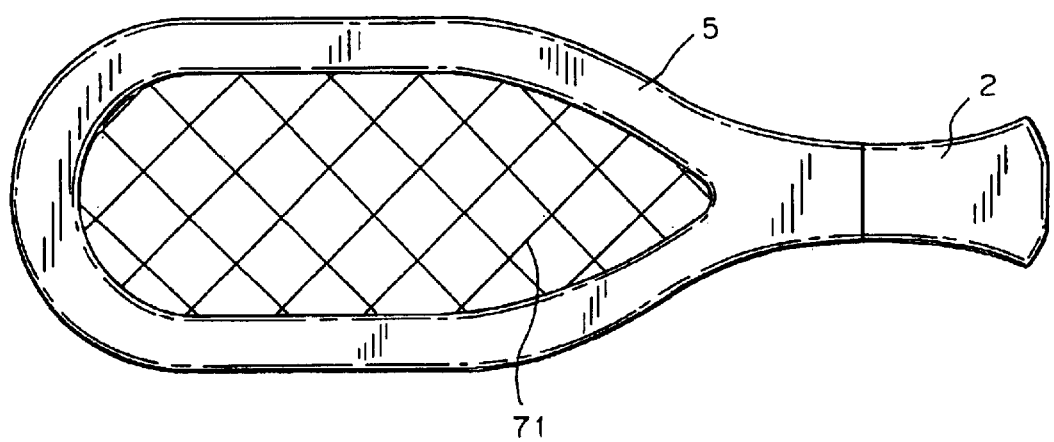
FIG. 7 shows an embodiment in which the wax removing member is in the form of a grid.

In the modified implement shown in FIG. 7, the struts 71 are in an intersecting pattern to create a grid for scraping wax from a surface of the ear canal, the wax entering the interstices of the grid and being scraped from the canal surface when the grid is swept thereover.

Figure 8:
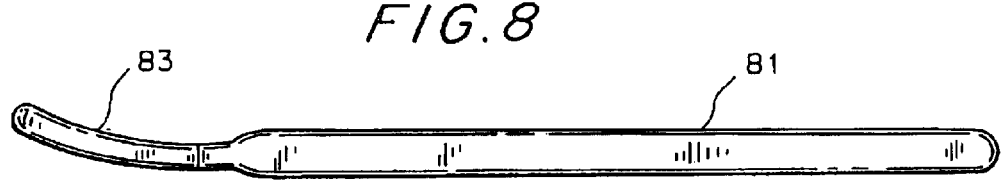
FIG. 8 shows an implement having a loop at one end of a straight stem, the loop being curved.

The modification shown in FIG. 8 applies to all embodiments of the implement disclosed herein. In this modification, the loop component 83 of the implement is curved whereas the stem or handle component 81 is straight.

Safety Stopper

Figure 9A:
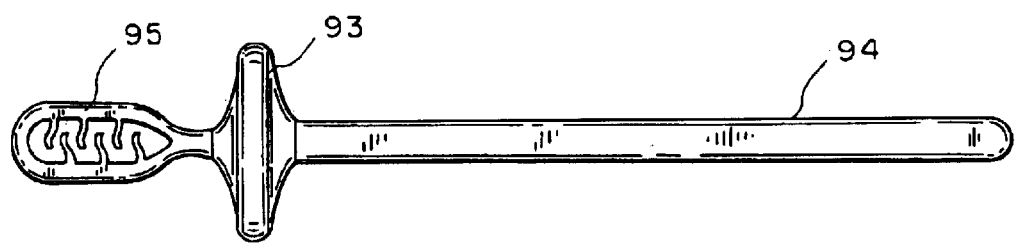
FIG. 9 illustrates an implement with a safety stopper to limit the extent to which the loop of the implement can be inserted in an ear canal.
Figure 9B:
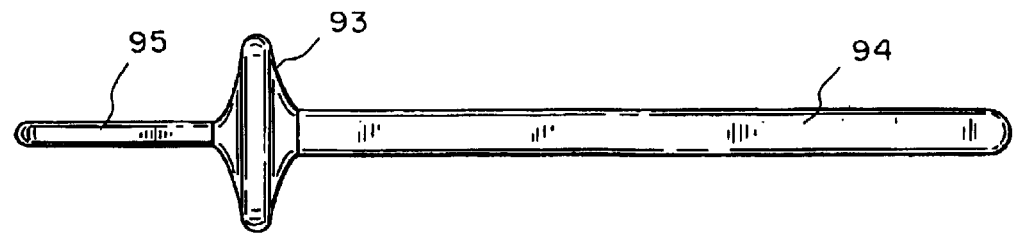

In order to limit the depth to which the loop of the implement can be inserted in an ear canal, in the implement shown in FIGS. 9a and 9b, there is included a safety stopper 93. Stopper 93 is placed at the junction of loop 95 and stem 94. Loop 95 is provided with inward projections forming a wax scraper, such as the wax scrapers shown in the first and second embodiments.

When loop 95 is inserted in an ear canal, the penetration of the loop therein is arrested by stopper 93 which engages the entry to the ear canal but is of greater width so that the stopper cannot be admitted.

It is fair to assume that not all users of an ear-cleaning implement having a stick-like handle will exercise care and therefore be careful not to insert the wax-removing element of the implement too deeply into the ear canal, thereby running the risk of damaging the ear drum at the end of the canal. The safety stopper included in the implement shown in FIGS. 9a and 9b is effective to prevent an excessive depth of penetration, whether the user of the implement is careful or careless.

Fourth Embodiment

In widespread use are double-headed cotton swabs, the swab at either end being adapted to remove wax from the ear canal or to absorb water therefrom. The drawback of a swab, when acting to remove wax, is that it tends to shove the wax further into the ear canal. The drawback of a swab, when used to absorb and store water, is that its water absorbing capacity is relatively small.

Both of these drawbacks are overcome in the double-headed ear hygiene implement shown in FIGS. 10 to 15 in which one head acts to scrape wax from the ear canal surface, the other to absorb water from the surface and to store it so that it can be removed from the ear. This double-headed implement is molded of a single piece of high-strength, biocompatible synthetic plastic material such as polypropylene or polyethylene. It includes an elongated flat shank 96 whose upper rim 97 is concave, the shank serving as the handle of the implement.

One end of shank 96 terminates in a tear-shaped loop 98 which defines the wax-removing head of the implement. The smooth rim of loop 98 merges through a hump 99 with one end of the upper rim 97 of the shank, the hump acting as a safety guard for the loop. The other end of shank 96 terminates in a tear-shaped loop 100 which defines the water-removing head of the implement. The rim of loop 100 merges via a safety-guard hump 101 with the other end of the upper rim 97 of the shank.

Wax-removing loop 98 is provided with wax removing members 102 and 103 projecting inwardly from opposite ends of the loop. In practice, these members may be of the type shown in the other embodiments of the implement.

As illustrated in FIG. 11, when a user U who grasps handle 96 of the implement and inserts loop 98 into canal C of an ear E, then guard 99 which engages the entry into the canal prevents loop 98 from going beyond the region in the canal having a wax coating. And when the implement is manipulated to sweep back and forth and massage the surface of the canal, loop 98 then scrapes the wax from this surface. The scraped off wax W adheres to and is collected by the inward projections 102 and 103, as shown in FIG. 12.

And as shown in FIG. 13, once wax W has been scraped off the surface of the canal and collected on the wax scraper within the loop, one now can remove the loop from the canal, for guard 99 prevents movement of the loop further into the canal. Because the loop is thin and flat, it cannot function as a piston to ram the surface wax further into the canal, as does a conventional bulbous cotton swab.

Loop 100 defining the water-removing head of the implement has mounted therein an initially flat pad 104 of cellulosic or other highly absorbent material having sponge-like characteristics, as shown in FIG. 14. The contours of pad 104 match those of the tear-shaped loop, the arrangement being such that the pad can be snapped into the loop.

The depth to which loop 100 can be inserted in ear canal C is limited by safety guard 101. When loop 100 is swept over a moisture-laden ear canal, the water is absorbed by pad 104, causing the pad to swell out like a sponge from either side of the loop as shown in FIG. 15. This sponge has a relatively large water storage capacity so that it is capable of absorbing and storing whatever water is entrapped in the ear canal.

A double-headed ear hygiene implement in accordance with the invention is a full service device, for it removes both wax and water from the ear and leaves the ear in a clean and healthy state. In practice, the double-headed implement may be designed only to remove wax, in which case both heads are wax scrapers, or designed only to remove water, in which case both heads are water absorbers.

It is to be noted that the loops 98 and 104 extending from opposite ends of the shank are upwardly curved to conform to the natural curvature of the ear canal, so that each loop slides smoothly into the ear canal.

Alternatively, the loops need not be planar but may be twisted relative to the plane of the shank 96 to follow the curvature of a spiral so that in effect one can screw the loop into an ear canal.

Pad 104 mounted within loop 100 is preferably composed of two like sections which are laminated together so that when the pad is wet, the pads then expand outwardly from opposite sides of the loop 100. This loop is provided with small inwardly-projecting teeth which pierce the pad and lock it in place so that it cannot be dislodged when the pad is put to use in the canal.

Instead of having a loop-mounted pad to absorb water, use may be made on one end of the implement of a short stem having a cotton ball wrapped thereabout as in a conventional cotton swab. Alternatively in place of a cotton ball, the absorbent material mounted in the short stem could be nipple-shaped as in a swab intended for a baby.

It is important to note that the double-headed implement shown in FIG. 10 has a two-dimensional flat form and that the safety guards 99 and 101 adjacent the respective loops 98 and 100 extend laterally from one side of the shank.

This flat configuration of the implement prevents rotation of a loop within an ear canal, for the hand grasping the shank of the implement can only turn in either direction a maximum of 180 degrees. This bidirectional restriction on movement of the implement is desirable in order to be able to sweep a loop back and forth in an ear canal to massage the canal surface and, in doing so, to scrape off and collect the wax therein.

Each guard adjacent a loop not only limits the degree to which the loop can be inserted in an ear canal but it also acts as a fulcrum about which the loop can sweep back and forth to massage the canal surface.

While there have been shown preferred embodiments of an ear hygiene implement, it is to be understood that many changes may be made therein without departing from the spirit of the invention. Thus the same implement can be used for cleaning nostrils.

What is claimed is:

1. An implement insertable into an ear canal to scrape wax from its surface without injuring the surface, paid implement comprising:
   A. a shank serving as a handle and terminating at one end in a loop having a smooth exterior so that the loop when inserted into the canal will then slide over the surface thereof; and
   B. a wax scraping member projecting inwardly into the loop lying in a plane passing through the loop, whereby when the implement is manipulated to cause the loop the sweep over the canal surface, the member will scrape the wax off the surface and collect it within the loop so that it can be removed from the canal
   wherein said loop and said wax scraping in member have substantially the same thickness, and said wax scraping member comprises a plurality of elements protecting inwardly into the loop.

2. The implement as set forth in claim 1, in which the inwardly projecting elements of the wax scraping member comprise edged teeth.

3. The implement as set forth in claim 2, in which the teeth are triangular.

4. The implement as set forth in claim 2, in which the teeth a e curved.

5. The implement as set forth in claim 1 in which the loop is paddle-shaped and said plurality of inwardly projecting elements of said wax-scraping in member form a plate having an array of edged holes therein.

6. The implement as set forth in claim 5, in which the holes are round.

7. The implement as set forth in claim 5, in which the holes are square.

8. The implement as set forth in claim 1, in which the member is formed by struts.

9. The implement as set forth in claim 1, further includes stopper interposed between the loop and the shank to limit the extent to which the loop can be inserted into the canal.

10. The implement as set forth in claim 1, in which the loop is flat and thin and therefore is incapable of ramming the wax further into the canal.

11. The implement, as in claim 1, further including a stern projecting from the other end of the shank on which is anchored a water-absorbing head to absorb moisture from the surface of the canal.

12. In an ear hygiene implement provided with a shank for supporting at either end thereof an element insertable into an ear canal having a curved entry, said shank comprising an elongated flat strip having an upper edge that is contoured to define adjacent either end thereof to which an element is attached a flat bump which acts to prevent the element from being admitted to the entry of the canal when the shank is not properly oriented, and acts top limit the degree to which when the element is admitted can be inserted into the ear canal.

13. The implement as in claim 12, in which the elements attached to both ends of the shank are wax-extracting elements.

14. The implement as set forth in claim 12, in which attached to one end of the shank is a moisture-absorbing element and to the other end a wax-extracting element.

15. The implement as set forth in claim 12, in which the elements attached to the ends of the shank are both water-absorbing elements.

16. A double-headed ear hygiene implement insertable into an ear canal, one head (X) functioning to scrape w x from the canal surface, the other head (Y) functioning to absorb water from the surface; each implement comprising:

A. a shank graspable by a user of the implement as a handle, said shank terminating at one end thereof in a loop defining the X-head an at an opposite end in a loop defining the Y-head;

B. said X-head being provided within an inwardly-projecting scraping member which lies in a plane extending through the loop thereof whereby the X-head is inserted in the canal and manipulated by the user to sweep the surface thereof, the wax is scraped therefrom and collected within the loop; and C. said Y-head being provided with a flat insert of absorbent material mounted within the loop thereof, whereby when the Y-head is inserted in the canal and manipulated by the user the sweep the surface thereof water is then absorbed by the insert to cause it to swell to store the absorbed water so that it can be removed from the canal.

17. An implement as set forth in claim 16, wherein said inwardly projecting scraper is formed by a plurality if edged teeth.

18. The implement as set forth in claim 17, wherein each loop is twisted with respect to the shank.

19. An implement as set forth in claim 16, in which the shank and the loops at opposite ends of the shank are molded of a ingle piece of biocompatible synthetic plastic material.

20. An implement as set forth in claim 16, in which the single piece is molded to define a flat shank and flat loops at the ends of the shank.

21. An implement as set forth in claim 16, in which said flat shank has a concave contour at its upper edge which merges with the loops.

22. An implement as set forth in claim 16, in which the upper edge of the shank merges with the loop at either end thereof via a hump serving as a guard to limit the extent to which he loop can be inserted in to the canal.

23. A double-headed ear hygiene implement insertable into an ear canal, said implement comprising:

A. a shank serving as a handle and terminating at either end in a loop having a smooth exterior so that the loop when inserted into the canal will then slide over te surface thereof; and B. a wax scraping member projecting inwardly into the loop and lying in a plane passing through the loop, whereby when the implement is manipulated to cause the loop to sweep over the canal surface, the member will scrape the wax off the surface and collect it within the loop so that it can be removed from the canal wherein said loop and said wax scraping member have substantially the same thickness, and said wax scraping member comprises a plurality of elements projecting inwardly into the loop.

24. An implement insertable into an ear canal to scrape wax from its surface without injuring the surface, said implement comprising:

A. a shank serving as a handle and terminating at one end in a loop having a smooth exterior so that the loop when inserted into the canal will then slide over the surface thereof; and B. a wax scraping member formed by edged teeth projecting inwardly into the loop and lying in a plane passing through the loop, wherein the teeth are triangular or curved, whereby when the implement is manipulated to cause the loop to sweep over the canal surface, the member will scrape the wax off the surface and collect it within the loop so that it can be removed from the canal.

25. An implement insertable into an ear canal to scrape wax from its surface without injuring the surface, said implement comprising:

A. a shank serving as a handle and terminating at one end in a loop having a smooth exterior so that the loop when inserted into the canal will then slide over the surface thereof, B. a wax scraping member projecting inwardly into the loop lying in a plane passing through the loop, whereby when the implement is manipulated to cause the loop the sweep over the canal surface, the member will scrape the wax off the surface and collect it within the loop so that it can be removed from the canal;

wherein the loop is paddle-shaped, and projecting inwardly from the loop is a plate having an array of round, edged holes therein, said wax scraping member comprising said plate.

* * * * *